(12) United States Patent
Stevens et al.

(10) Patent No.: US 7,405,417 B2
(45) Date of Patent: Jul. 29, 2008

(54) LITHOGRAPHIC APPARATUS HAVING A MONITORING DEVICE FOR DETECTING CONTAMINATION

(75) Inventors: Lucas Henricus Johannes Stevens, Eindhoven (NL); Vadim Yevgenyevich Banine, Helmond (NL); Johannes Hubertus Josephina Moors, Helmond (NL); Bastiaan Theodoor Wolschrijn, Abcoude (NL)

(73) Assignee: ASML Netherlands B.V., Veldhoven (NL)

( * ) Notice: Subject to any disclaimer, the term of this patent is extended or adjusted under 35 U.S.C. 154(b) by 223 days.

(21) Appl. No.: 11/311,624

(22) Filed: Dec. 20, 2005

(65) Prior Publication Data

US 2007/0138414 A1    Jun. 21, 2007

(51) Int. Cl.
*G01J 3/10* (2006.01)
*G01N 21/88* (2006.01)
*G03B 27/72* (2006.01)

(52) U.S. Cl. .............. 250/504 R; 250/365; 250/370.08; 250/370.09; 250/372; 250/461.1; 359/350

(58) Field of Classification Search ............ 250/504 R, 250/307.09
See application file for complete search history.

(56) References Cited

U.S. PATENT DOCUMENTS

| | | | | |
|---|---|---|---|---|
| 4,574,194 A * | 3/1986 | Coats et al. | ................. | 250/308 |
| 5,487,981 A * | 1/1996 | Nivens et al. | ................. | 435/30 |
| 6,545,272 B1 * | 4/2003 | Kondo | ........................ | 250/305 |
| 6,649,403 B1 * | 11/2003 | McDevitt et al. | ......... | 435/288.5 |
| 6,724,460 B2 * | 4/2004 | Van Schaik et al. | ........... | 355/30 |
| 6,828,569 B2 * | 12/2004 | Van Schaik et al. | ...... | 250/492.2 |
| 6,906,777 B1 * | 6/2005 | Kye et al. | .................... | 355/30 |
| 6,924,492 B2 * | 8/2005 | Van Schaik | .............. | 250/492.1 |
| 6,980,281 B2 * | 12/2005 | Moors et al. | .................. | 355/67 |
| 7,012,265 B2 * | 3/2006 | Van Der Veen | .......... | 250/492.2 |
| 7,064,324 B2 * | 6/2006 | Onishi | ........................ | 250/310 |
| 7,115,886 B2 * | 10/2006 | Van Schaik et al. | ...... | 250/492.2 |
| 7,116,394 B2 * | 10/2006 | Bakker et al. | ................. | 355/30 |
| 7,142,287 B2 * | 11/2006 | Kroon et al. | .................. | 355/71 |
| 7,145,641 B2 * | 12/2006 | Kroon et al. | .................. | 355/71 |
| 7,156,925 B1 * | 1/2007 | Subramanian et al. | ......... | 134/1 |
| 7,230,674 B2 * | 6/2007 | Kroon et al. | .................. | 355/30 |
| 2002/0037461 A1 * | 3/2002 | Van Der Werf et al. | ....... | 430/30 |
| 2002/0083409 A1 | 6/2002 | Hamm | | |
| 2004/0130694 A1 * | 7/2004 | Kurt et al. | ...................... | 355/69 |
| 2004/0227102 A1 * | 11/2004 | Kurt et al. | ................ | 250/491.1 |

(Continued)

FOREIGN PATENT DOCUMENTS

EP        1 452 851 A1    9/2004

(Continued)

*Primary Examiner*—David A. Vanore
*Assistant Examiner*—Bernard Souw
(74) *Attorney, Agent, or Firm*—Pillsbury Winthrop Shaw Pittman, LLP (57) ABSTRACT

A lithographic apparatus is disclosed. The apparatus includes a projection system configured to project a first radiation beam onto a target portion of a substrate, and at least one monitoring device for detecting contamination in a interior space. The monitoring device includes at least one dummy element having at least one contamination receiving surface. In an aspect of the invention, there is provided at least one dummy element which does not take part in transferring a radiation beam onto a target portion of a substrate, wherein it is monitored whether a contamination receiving surface of the dummy element has been contaminated.

36 Claims, 6 Drawing Sheets

U.S. PATENT DOCUMENTS

| | | | |
|---|---|---|---|
| 2005/0133727 A1* | 6/2005 | Banine et al. | 250/397 |
| 2005/0140956 A1* | 6/2005 | Kroon et al. | 355/71 |
| 2006/0066824 A1* | 3/2006 | Knappe et al. | 355/30 |
| 2007/0115443 A1* | 5/2007 | Box et al. | 355/30 |
| 2007/0115445 A1* | 5/2007 | Box et al. | 355/30 |
| 2007/0132989 A1* | 6/2007 | Kaller et al. | 356/239.1 |
| 2007/0138414 A1* | 6/2007 | Stevens et al. | 250/504 R |
| 2007/0242247 A1* | 10/2007 | Shiraishi | 355/53 |
| 2007/0291239 A1* | 12/2007 | Shiraishi | 355/30 |

FOREIGN PATENT DOCUMENTS

JP  407153634 A * 6/1995

* cited by examiner

LITHOGRAPHIC APPARATUS HAVING A MONITORING DEVICE FOR DETECTING CONTAMINATION

FIELD

The present invention relates to a lithographic apparatus that includes a monitoring device for detecting contamination. The present invention also relates to an apparatus and a method for detecting contamination and a method for manufacturing a device.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of one, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In case of an interior space of the apparatus, for example a vacuum space, it is generally desired to monitor the interior space for contamination. This is the case, for example, when the interior space is used in a lithographic process, or, for instance, when the space is included in a lithographic apparatus. In that case, it is desired to detect contamination quickly—preferably within a fraction of a second—so that a lithographic process can be halted immediately, to prevent contamination sensitive optics being spoiled by the contamination. For example, the lithographic process can be halted by stopping the exposure, by stopping a radiation source and/or by closing a shutter in the path of the radiation beam. However, the interior space can also be applied in different fields, for instance general semiconductor industry, general vacuum technology industry, space technology and the-like. The present invention can therefore also explicitly be applied outside the field of lithography.

United States Patent Application Publication No. 2002/0083409 A1 relates to EUV lithography devices and processes, wherein a quartz crystal microwave is use as a measuring device.

European Patent Application Publication No. EP 1 452 851 A1 relates to a method and device for measuring contamination of a surface of a component of a lithographic apparatus. The measuring device has a radiation transmitter device for projection radiation on at least a part of said surface and a radiation receiver device for receiving radiation from the component.

SUMMARY

It is desirable to provide an improved apparatus and method for monitoring contamination, wherein the occurrence of contamination can be detected swiftly, using a relatively simple, inexpensive monitoring device.

According to an aspect of the invention, there is provided a lithographic apparatus, comprising a projection system configured to project a first radiation beam onto a target portion of a substrate, the lithographic apparatus further including at least one monitoring device for detecting at least one contamination species in an interior space of the apparatus, wherein the monitoring device includes at least one dummy element having at least one contamination receiving surface, which contamination receiving surface is in contact with said interior space, wherein the at least one monitoring device includes at least one emitter configured to emit a second radiation beam, which second radiation beam is projected at least partially onto the contamination receiving surface of said dummy element, and wherein the monitoring device includes a detector which is constructed to detect whether the at least one contamination receiving surface of the dummy element has been contaminated.

In an aspect of the invention, there is provided a lithographic apparatus, comprising a projection system configured to project a first radiation beam onto a target portion of a substrate, the lithographic apparatus further including at least one monitoring device for detecting at least one contamination species in an interior space of the apparatus, wherein the monitoring device includes at least one dummy element having at least one contamination receiving surface, which contamination receiving surface is in contact with said interior space, wherein the at least one monitoring device includes at least one emitter configured to emit a second radiation beam, which second radiation beam is projected at least partially onto the contamination receiving surface of said dummy element, and wherein said dummy element is at least partially transparent to the radiation of said at least second radiation beam. The monitoring device can include a first detector which is arranged to receive a part of said second radiation beam which is being transmitted and/or reflected by said dummy element.

In an aspect of the invention, there is provided a lithographic apparatus, comprising a projection system configured to project a first radiation beam onto a target portion of a substrate, the lithographic apparatus further including at least one monitoring device for detecting at least one contamination species in an interior space of the apparatus, wherein the monitoring device includes at least one quartz crystal monitor or surface acoustic wave detector having at least one contamination receiving surface, which contamination receiving surface is in contact with said interior space, wherein the at least one monitoring device includes at least one emitter configured to emit a second radiation beam, which second radiation beam is projected at least partially onto the contamination receiving surface. The quartz crystal monitor or surface acoustic wave detector is configured to detect whether the at least one contamination receiving surface has been contaminated.

In an aspect of the invention, there is provided a lithographic apparatus, comprising a projection system configured to project a first radiation beam onto a target portion of a substrate, the lithographic apparatus further including at least one monitoring device for detecting at least one contamination species in an interior apparatus space, wherein the monitoring device includes at least one dummy element having at least one contamination receiving surface, which contamination receiving surface is in contact with said interior space, wherein the at least one monitoring device includes at least one emitter configured to emit an electron beam or ionising beam, which electron beam or ionising beam is projected at least partially onto the contamination receiving surface of said dummy element. The monitoring device can include a detector which is constructed to detect whether the at least one contamination receiving surface of the dummy element has been contaminated.

In an aspect of the invention, there is provided a lithographic apparatus arranged to transfer a pattern from a patterning device onto a substrate, utilizing at least one interior space, for example a vacuum, wherein the apparatus includes at least one dummy element which does not take part in transferring said pattern onto said substrate, wherein the dummy element is contact with said interior space, wherein the apparatus includes at least one radiation emitter for irradiating said dummy element with radiation, which radiation serves to modify, crack and/or detect contamination which the dummy element can receive from said interior space.

In an aspect of the invention, there is provided a method for monitoring contamination in an interior space used in a lithographic process, the method including: providing at least one dummy element which does not take part in transferring a first radiation beam onto a target portion of a substrate; wherein a contamination receiving surface of the dummy element is in contact with said interior space for receiving said contamination, if any, therefrom, wherein it is monitored whether the contamination receiving surface has been contaminated by said contamination.

Also, according to an aspect of the invention, there is provided a lithographic apparatus, including: a number of optical elements configured to project a first radiation beam onto a target portion of a substrate; at least one radiation source which is configured to emit a second radiation beam; a radiation beam controller configured to direct the second radiation beam onto at least one surface part of at least one of said optical elements; and at least one detector which is configured to detect electrical current, which current emanates from said at least one surface part of said optical element when that surface part interacts with said second radiation beam.

According to an aspect of the invention, there is provided a method for monitoring contamination of an optical element, the method comprising: projecting a beam of radiation onto at least one surface part of said optical element, to generate an electrical monitoring current in the element; measuring said electrical monitoring current.

According to an aspect of the invention, there is provided a lithographic device manufacturing method, comprising: providing a projection system which projects a first radiation beam onto a target portion of a substrate, the projection system including at least one optical element; projecting a second beam of radiation onto at least one surface part of said optical element, to generate an electrical monitoring current in the element; and measuring said electrical monitoring current.

In an aspect of the invention, there is provided a method for monitoring contamination of at least one optical element, the method comprising: scanning a beam of radiation over a surface of said optical element for producing an electrical monitoring current in the element via the photo-electric effect; measuring said electrical monitoring current.

Further, according to an aspect of the invention, there is provided a device manufacturing method comprising projecting a patterned beam of radiation onto a substrate, utilizing a number of optical elements, wherein the device manufacturing method includes: scanning a second beam of radiation over a surface of said optical element for producing an electrical monitoring current in the element; measuring said electrical monitoring current.

According to an aspect of the invention, a system for monitoring contamination of an optical mirror element includes: at least one radiation source which is configured to emit a radiation beam; a radiation beam controller configured to direct the radiation beam towards different locations of a surface of at least one of said optical elements; and at least one detector which is configured to detect electrical current, which current emanates from said optical element when the optical element interacts with said second radiation beam.

According to an aspect of the invention, there is provided a computer program product comprising computer code portions, configured to be run on the processor of a system for monitoring contamination of an optical mirror element: to detect deviations or changes of the current, measured by said at least one detector; and/or to process and/or store measurement results, which results include electrical current measured by said detector when said second radiation beam is being projected onto said optical element, and the respective location of said surface part of said optical element which receives the radiation beam.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

In the present description, equal or similar features can be referred to by equal or similar reference signs.

Figure 1:
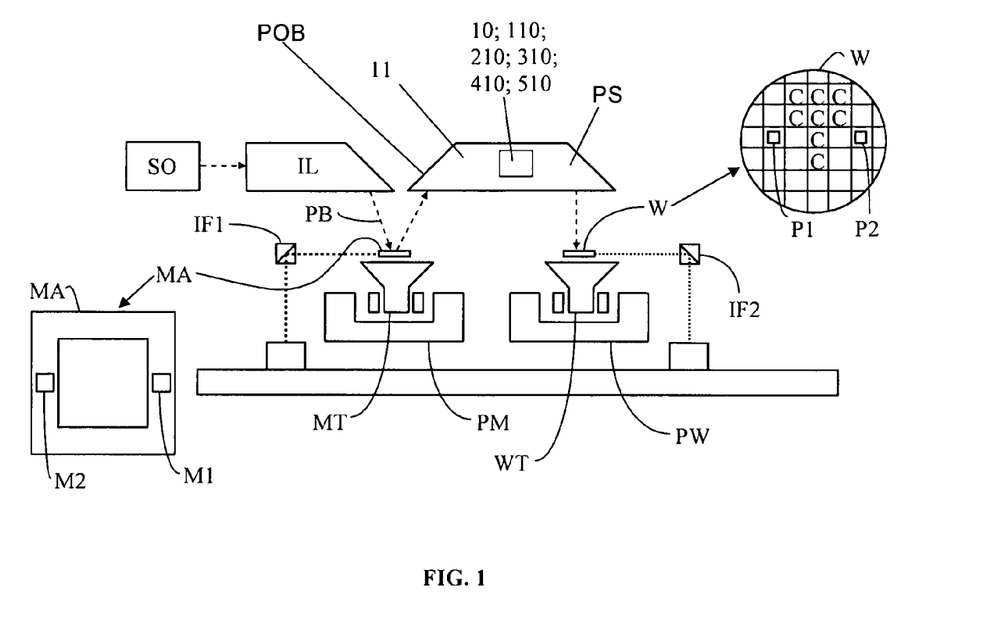
FIG. 1 depicts a lithographic apparatus according to an embodiment of the invention.

FIG. 1 schematically depicts a lithographic apparatus according to one embodiment of the invention. The apparatus comprises: an illumination system (illuminator) IL configured to condition a beam of radiation (e.g. UV radiation or other radiation); a support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to a—conditioned—first radiation beam PB by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system". The projection system can, for example, be located in a so called projection optics box POB.

As here depicted, the apparatus is of a reflective type (e.g. employing a reflective mask). Alternatively, the apparatus may be of a transmissive type (e.g. employing a transmissive mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives an unconditioned beam of radiation from a radiation source SO. The source and the lithographic apparatus may be separate entities, for example when the source is an excimer laser. In such cases, the source is not considered to form part of the lithographic apparatus and the beam of radiation is passed from the source SO to the illuminator IL with the aid of a beam delivery system comprising, for example, suitable directing mirrors and/or a beam expander. In other cases the source may be an integral part of the lithographic apparatus, for example when the source is a mercury lamp. The source SO and the illuminator IL, together with the beam delivery system if required, may be referred to as a radiation system.

The illuminator may be used to condition the beambeam of radiation emitted by the source SO, to have a desired uniformity and intensity distribution in its cross-section. The illuminator IL may comprise an adjuster for adjusting the angular intensity distribution of the beam of radiation. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator and a condenser.

The—conditioned—first radiation beam PB is incident on the patterning device (e.g., mask MA), which is held on the support structure (e.g., mask table MT), and is patterned by the patterning device. Having traversed the mask MA, the first radiation beam PB passes through the projection system PS, which focuses the first beam onto a target portion C of the substrate W. With the aid of the second positioner PW and position sensor IF2 (e.g. an interferometric device, linear encoder or capacitive sensor), the substrate table WT can be moved accurately, e.g. so as to position different target portions C in the path of the patterned first radiation beam PB. Similarly, the first positioner PM and another position sensor IF1 can be used to accurately position the mask MA with respect to the path of the first radiation beam PB, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the first radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the first radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the first radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

As FIG. 1 schematically shows, an interior space 11 of the apparatus can include at least one monitoring device 10, 110, 210, 310, 410, 510 for monitoring contamination. The monitoring device 10, 110, 210, 310, 410, 510 can be located in various locations of the device, for example in or near the projection system, in the projection optics box POB, in a reticle zone, in a substrate zone, the illuminator IL or in other locations of the apparatus.

The interior space 11 can be located, for example in a vacuum chamber. The interior space 11 can be, for example, a vacuum space. The vacuum of the vacuum space cap have varying vacuum pressures, which can depend, for example, on the radiation type of the first radiation beam PB used in the lithographic apparatus. Alternatively, the interior space can be an immersion liquid space which is filled with an immersion fluid during use. Also, an interior space that has been provided with at least one monitoring device 10 can be, for example, a space which also contains the patterning means, a space which also contains the substrate support, or an other space of the apparatus. The interior space can also have an atmospheric pressure, or a different pressure.

Figure 2:
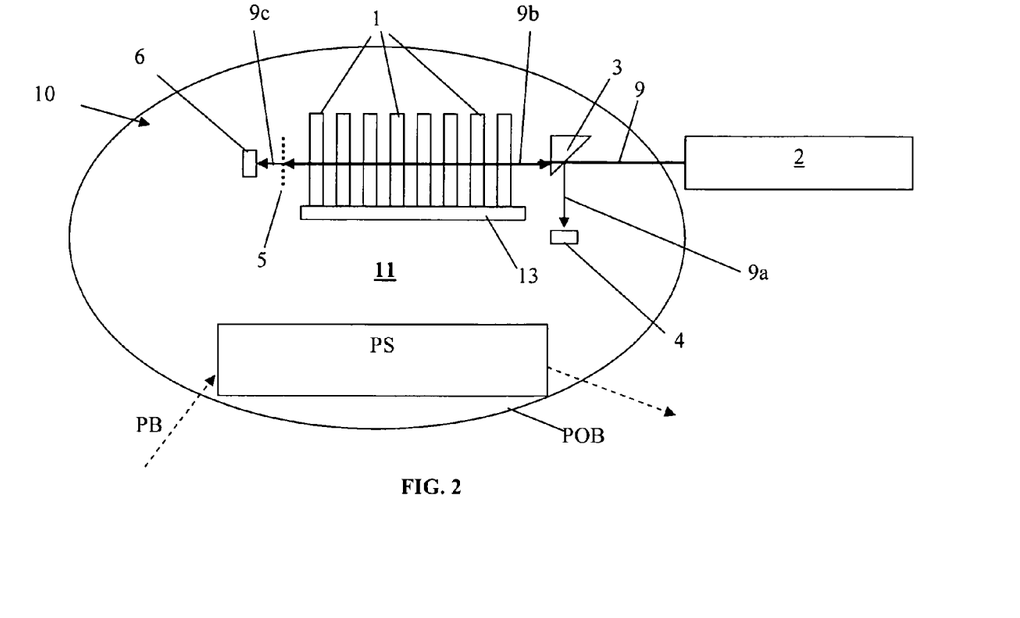
FIG. 2 schematically shows a first embodiment of a contamination monitoring device.

FIG. 2 schematically shows a first embodiment of an above-mentioned contamination monitoring device 10, which can be located in an interior space for monitoring contamination, for example in an interior of a lithographic apparatus, for example in an apparatus as shown in FIG. 1 or in an other apparatus.

The monitoring device 10 can be arranged to detect at least one contamination species in the interior apparatus space 11. In the embodiment of FIG. 2, the monitoring device is installed in a lithography projection optics box POB, which box POB comprises said interior space 11. This optical box POB can include at least part of said projection system PS. This projection system PS can also be in contact with the interior space 11 during use.

The monitoring device 10 can include at least one dummy element 1 having at least one contamination receiving surface. The dummy element 1 does not take part directly in transferring a radiation beam onto a target portion of a substrate during a lithographic process. For example, the above-mentioned first radiation beam PB is preferably not being projected onto the dummy element 1 during use. The monitoring device can comprise for example a plurality of dummy elements 1 (as is shown in FIG. 2), for example at least 20 dummy elements 1, or a different number of dummy elements 1.

In the embodiment of FIG. 2, each dummy element 1 extends substantially within the interior apparatus space 11. Therefore, the contamination receiving surface of each dummy element 1 is in contact with said interior space 11 during use. Thus, during use each dummy element 1 can be contaminated by the same contamination as the projection system PS, for the case that contamination is present in the interior space 11.

The monitoring device 10 further can include at least one emitter 2 which is configured to emit a second radiation beam 9. This second radiation beam 9 is projected at least partially onto the contamination receiving surface of said dummy element 1 during use. For example, this second radiation beam 9 is preferably not being projected onto the projection system PS during use (see FIG. 2).

The radiation of said at least second radiation beam 9 can be selected, for example, from the group consisting of the following radiation types: visible light, infra red light, ultra violet light, Deep UV light, extreme ultra-violet light and microwave radiation. The radiation can be chosen, for example, to modify or crack at least one contamination species into one or more compounds having improved absorbability to the second radiation beam 9. The radiation type of the second radiation beam 9 can be chosen, for example, to cause carbonization of said dummy element 1 in case the apparatus interior space 11 contains hydrocarbon contamination. For example, an Ultra Violet (UV) second radiation beam 9 can be used, which can crack certain hydrocarbon contamination into better detectable matter, which matter leads to the carbonization of the dummy elements 1. Good carbonization can also be achieved by using a second radiation beam 9 of microwave radiation or electron beam radiation.

The cracking of the at least one contamination species can also resemble the process, for example when it takes place in the projection beam PB during illumination. It can also to have a continuing effect, for example: adsorption can stop while the contamination can continue.

Also, the radiation beam can be a beam of visible light, or infrared light. Visible light or infrared light is relatively easy producible, with inexpensive means.

Besides, there could be used two beams at once, for example a first beam to cause a reaction and/or modification of contamination, and a second beam to measure the effect of the reacted and/or modified contamination.

The radiation emitter 2 can be designed in various ways. For example, the radiation emitter can be a laser, an electron beam emitter, or a different type of radiation emitter.

In the embodiment of FIG. 2, each dummy element 1 is at least partially transparent to the radiation of said at least second radiation beam 9. For example, each dummy element 1 can be substantially transparent to that radiation. For example, the at least one dummy element 1 can be made of glass, a transparent plastic, quartz or calcium fluoride for IR, et cetera. Alternatively, said contamination receiving surfaces of said dummy elements 1 can reflect substantially all radiation of said second radiation beam during use, which is described below with reference to FIG. 3.

Each dummy element 1 can have various shapes. For instance, each dummy element can be a rod-like or plate-like element, or a differently shaped element. For example, two surfaces of each said dummy element 1, which two surfaces are substantially faced away from each other, can serve as contamination receiving surfaces during use, as is shown in the embodiment of FIG. 2.

In an aspect of the invention, said monitoring surface of each dummy element 1 includes the same material as a radiation receiving surface, or an outer material, of said projection system PS. In that case, each contamination receiving surface of each dummy element 1 can have about the same sensitivity to certain contamination types as surfaces of the projection system PS.

The at least one dummy element 1 can be constructed to provide an array of contamination receiving surfaces, wherein at least part of said at least second radiation beam passes all of the contamination receiving surfaces of said array at least once during use. The monitoring device can also include a plurality of said dummy elements 1 which provide a plurality of contamination receiving surfaces that are spaced-apart from each other. Contamination receiving surfaces of neighbouring dummy elements can be located opposite one another.

In the embodiment of FIG. 2, the contamination monitor 10 includes an above-mentioned array of dummy elements 1. This array provides an array of contamination receiving surfaces, each of which is in contact with said interior apparatus space 11. At least part 9b of said at least second radiation beam 9 passes all of the contamination receiving surfaces of said array at least once during use. In the embodiment of FIG. 2, the contamination receiving surfaces are formed by the outer surfaces of the dummy elements 1 which extend substantially parallel to each other. Alternatively, for example, at least a number of the contamination receiving surfaces can extend in a non-parallel fashion with respect to each other.

During use of the embodiment of FIG. 2, part 9b of the second radiation beam passes each radiation receiving surface substantially perpendicularly, to provide a short pathlength of that radiation passing through a respective dummy element 1. This can provide a high transmission ratio of transmission of the radiation through the dummy element 1. Alternatively, part 9b of the second radiation beam can pass one or more radiation receiving surfaces in a non-perpendicular manner. This can result in a higher sensitivity to the contamination layer.

By providing a plurality of subsequent contamination receiving surfaces (see FIG. 2 or 3), the contamination sensitivity of the contamination monitor can be greatly enhanced.

At least one radiation reflector can be provided, which reflector is arranged to reflect radiation of said at least second radiation beam 9 at least partially towards said contamination receiving surface of said dummy element 1. As an example only, said dummy element 1 can be located between at least two radiation reflectors, wherein the reflectors are arranged to reflect radiation of said second radiation beam towards each other, through said dummy element. Then, at least part of the radiation beam can be passed a plurality of times towards the contamination receiving surface or surfaces of said at least one dummy element, for enhancing contamination sensitivity. In the embodiment of FIG. 2, the array of dummy elements 1 is located between two radiation reflectors 3, 5. The reflectors 3, 5 are arranged to reflect radiation of said second radiation beam towards each other, through said dummy elements 1. The radiation reflectors 3, 5 can be arranged in various ways, and can be made of various suitable materials, as will be clear to the skilled person.

For example, the first reflector 3, which is located between one side of the dummy elements 1 and the radiation emitter 2, can be arranged to reflect a major part of incoming radiation, received from the dummy elements 1, back towards the dummy elements 1. The second reflector 5, which is arranged between the opposite side of dummy elements 1 and a second detector 6, can be arranged to reflect only part of incoming radiation back towards the dummy elements 1, and to transmit the remaining beam part 9c towards the second detector 6. In that case, the second reflector 5 is a partial reflector.

The monitoring device can further include a detector which is constructed to detect whether the at least one contamination receiving surface of the dummy element has been contaminated.

The embodiment of FIG. 2 is provided with a first radiation detector 4 and a second radiation detector 6. The first detector 4 is arranged to receive a part 9a of said second radiation beam 9 directly, without that beam part 9a being transmitted and/or reflected by said dummy element 1. The second detector 6 is arranged to receive a part of said second radiation beam after that radiation beam has been transmitted by said dummy element 1 during use. For example, the second detector 6 is located downstream with respect to the array of dummy elements, to receive said second radiation beam 9c after the second radiation beam has been transmitted once or several times through the contamination receiving surfaces of said dummy elements 1. From radiation detection results, that can be provided by the second detector 6 during use, an absorption amount concerning absorption of radiation 9b of the second radiation beam 9 during the passing of the dummy elements 1, can be determined. Herein, for example, the absorption of radiation 9b can be determined, from which determination the amount of contamination can be determined. Alternatively, from radiation detection results, of the second detector 6, it can be determined, whether any change in radiation absorption has occurred during the passing of the dummy elements 1.

The detection results of the first detector 4 and second detector 6 can be compared with each other to determine, in what amount radiation 9b of the second radiation beam 9 has been absorbed during the passing of the dummy elements 1, or whether a change in incident radiation has occurred. The results of the first detector 6 can be used, for example, as a reference concerning detection results of the second detector 4. Also, the first detector 4 can be used to calibrate the second detector 6, for example when no contamination is present yet in the apparatus interior space 11.

The first and second detector can be arranged in various ways, which depends on the type of radiation to be detected. For example, one or both detectors can include at least one photo diode. Also, one or both detectors can be constructed to detect electrons. Also, one or both detectors can be designed to detect one or more of the above-mentioned radiation types.

The apparatus can also include a beam splitter 3, which is arranged to split the second radiation beam 9 into a first beam part 9a and a second beam part 9b. In the present embodiment, the beam splitter 3 and the first radiation reflector are integrated with each other. For example, the beam splitter can direct the incoming first beam part 9a towards the first radiation detector 4, and the second beam part 9b towards the possibly contaminated radiation receiving surface of the nearest of the dummy elements 1 (see FIG. 2).

Further, the monitoring device 10 can include a thermal controller 13 which controls the temperature of one or more dummy elements 1 during use. The thermal controller 13 can be arranged to cycle the temperature of one or more dummy elements 1 between a plurality of monitoring temperatures. To the skilled person, it will be clear that the thermal controller 13 can be constructed in various ways. The thermal controller can comprise, for example, one or more electric heaters, a heat exchanging fluid, a heat pipe and/or an other type of temperature controlling device. Also, for example, different dummy elements can be held at different constant temperatures, for example by the thermal controller.

In an aspect of the invention, a method for monitoring contamination in a lithographic process includes: providing at least one dummy element which does not take part in transferring a radiation beam onto a target portion of a substrate.

This method will now be explained, with reference to the embodiment of FIG. 2, as an example of the invention.

During a use of the embodiment of FIG. 2, the contamination receiving surfaces of dummy elements 1 are in contact with the interior space 11 for receiving contamination, if any, therefrom. Then, it is monitored whether the contamination receiving surfaces have been contaminated by one or more contamination species. To this aim, at least one second radiation beam 9 is being emitted by the radiation emitter 2. The second radiation beam 9 can be emitted continuously, in short radiation pulses and/or in any other way. Downstream of the emitter 2, the emitted radiation beam 9 is being split by beam splitter 3 into a first beam part 9a, which is projected onto the first detector 4, and into a second beam part 9b, which is being projected onto the array of dummy elements 1. The first beam part 9a is being detected by the first detector 4.

The second beam part 9b is being transmitter through the array of dummy elements 1, towards the second reflector device 5. The second reflector 5 reflects part of the incoming radiation back towards the first reflector 3, and transmits a remaining radiation part 9c to the second radiation detector 6, which detects the radiation. The latter beam part 9c contains radiation that has traversed the dummy elements 1 only once, and also radiation that has been reflected between the two opposite reflectors 3, 5 and that has therefore traversed the dummy elements 1 more than once. Therefore, part of the second radiation beam 9 can be projected a plurality of times onto contamination receiving surfaces of the dummy elements 1, after which that beam part is being detected by the second detector 6.

As long as the contamination receiving surfaces of the dummy elements 1 are substantially not contaminated during use, the second radiation detector 6 will detect a certain first amount of radiation. Once a number of the surfaces of the dummy elements are being contaminated, a change of radiation will be detected by the second radiation detector 6, which may trigger an alarm or a different action. Also, for example, a certain ratio between a signal of the first detector 4 and a signal of the second detector 6 can be used to trigger the alarm and/or to trigger an other action.

When a plurality of dummy elements 1 is being used for transmitting the second radiation beam, contamination can be detected swiftly, because of the cumulative effect on radiation absorption at the radiation receiving surfaces of the dummy elements 1. In that case, for example, the contamination can be detected at an early stage, before the contamination can do major harm to the projection system PS. When the contamination monitor 10 has detected the presence of contamination, it can trigger an alarm, an automatic halt of a lithographic process and/or an automatic stop of the emission of the first radiation beam PB. Then, damage to the projection system due to the first radiation beam PB illuminating contaminated parts of the projection system PS, can be prevented.

For example, when at least 20 dummy elements 1 are provided, at least twice that amount, i.e. at least 40 contamination receiving surfaces will be available, leading to a cumulative sensitivity improvement of 40× with respect to the use of one contamination receiving surface only.

The detection of changes in radiation transmission through the array of dummy elements 1 can be achieved with or without using the detection results of the first radiation detector 4. By using the results of the first radiation detector 4, a reliable contamination monitoring can be provided.

Hydrocarbon contamination is relatively harmful to optics of the projection system PS. Therefore, it is desirable to detect such hydrocarbon contamination fast, before it can do harm to the projection system PS by carbonizing parts of that system (for example under the influence of the first radiation beam PB).

In an aspect of the invention, said second radiation beam 9 modifies and/or cracks contamination that is present on or near said contamination receiving surface. For example, hydrocarbons can be cracked by the radiation beam 9, provided that a suitable cracking radiation type is used. Also, said monitoring surface of each dummy element 1 can include the same material as a radiation receiving surface of said projection system PS. Then, by providing a plurality of contamination receiving surfaces of dummy element(s) 1, these surfaces can be carbonized due to hydrocarbons present in the apparatus interior space 11. The cumulative effect of the carbonization of the plurality of the contamination receiving surfaces can be detected relatively early, for example before any surface of the projection system PS has been carbonized too much to necessitate projection system cleansing or repair. In an embodiment of the invention, the second radiation beam can be turned on before the radiation source SO of the projection system PS is switched on. Then, only when no change in radiation transmission through the dummy elements 1 is being detected, the radiation source SO of the projection system PS can be switched on safely.

The contamination monitor 10 can also be used to detect other contamination types, for example to detect water.

For example, the temperature of said dummy element 1 can be controlled to a certain temperature. The temperature of said dummy element can be cycled between a plurality of monitoring temperatures, for instance at least to a monitoring temperature at which certain contamination condenses onto the contamination receiving surface(s). In an aspect of the invention, a lithographic process includes the use of a projection system which transfers a patterned radiation beam onto a target portion of a substrate, wherein said monitoring surface of said dummy element includes the same material as a radiation receiving surface of said projection system. In that case, any undesirable effects of contamination to the projection system can be substantially the same as contamination effects that can be detected via the dummy element. This makes the dummy element a useful indicator for monitoring the presence of undesired species in the apparatus during the lithographic process.

Figure 3:
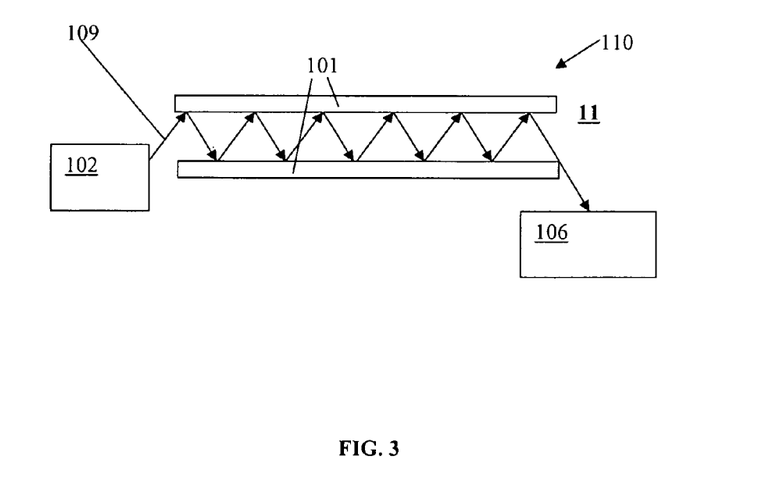
FIG. 3 schematically shows a second embodiment of a contamination monitoring device.

FIG. 3 depicts an embodiment of the invention, which differs from the embodiment of FIG. 2 in that the at least one dummy element 101 is arranged to reflect substantially all radiation of the second radiation beam 109. Also, said contamination receiving surface of said dummy element reflects substantially all radiation of a second radiation beam 109 during use. A detector 106 is arranged to receive said second radiation beam 109 after the second radiation beam 109 has been reflected at least once by the contamination receiving surface of said dummy element.

In the embodiment of FIG. 3, the dummy element 101 comprises two opposite dummy reflecting surfaces, each of which provides a contamination receiving surface that is in contact with the apparatus interior space 11 during use. During use, the second radiation beam 109 is reflected a plurality of times between the two dummy reflecting surfaces, as is indicated in FIG. 3. For example, the second radiation beam 109 can be reflected at least 20 times by each of the two reflecting surfaces, before that beam 109 is being detected by the radiation detector 106. In this way, the radiation beam 109 has been reflected at least 40 times by a contamination receiving surface, so that the second radiation beam can be cumulatively affected by contamination that has been received on those surfaces. This leads to a desirable enhancement of the sensitivity of the contamination monitor 110.

In an aspect of the invention, the apparatus includes at least a second emitter configured to emit a third radiation beam. The wavelength of the third radiation beam can differ from the wavelength of the second radiation beam. The third radiation beam is also projected at least partially onto the contamination receiving surface of said dummy element during use, particularly for modifying or cracking said contamination species into one or more compounds having improved absorbability of radiation of said second radiation beam.

For example, the second radiation beam can be projected onto the contamination receiving surface for the detection of contamination. The radiation type of the second radiation beam can be specifically chosen for allowing a relatively uncomplicated monitoring of the contamination receiving surface. For example, the second radiation beam can be a light beam of visible light, a laser beam, or an other suitable radiation beam.

Figure 4:
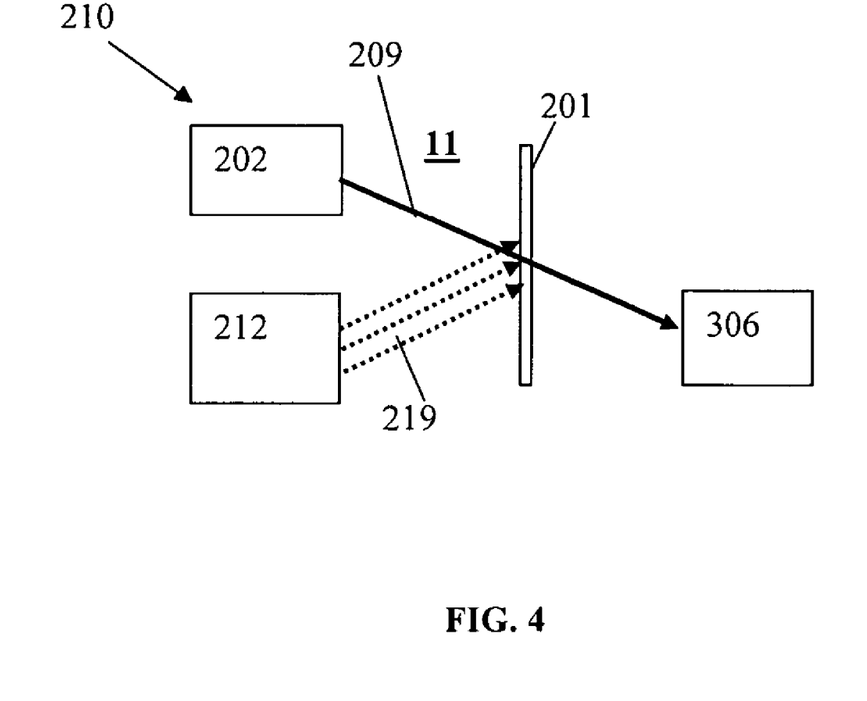
FIG. 4 schematically shows a third embodiment of a contamination monitoring device.

FIG. 4 shows an embodiment, wherein a further radiation emitter 212 is provided for emitting an above-mentioned third radiation beam 219. The third radiation beam 219 is projected onto the contamination receiving surface of at least one dummy element 201 (only one such element is shown in FIG. 4). The type of radiation of the third beam 219 can be specifically chosen to modify or crack at least one species into one or more compounds having improved absorbability of radiation of said second radiation beam. For example, the third radiation beam can be of a radiation type which can crack hydrocarbons.

During use, the second radiation beam 209 is emitted by the respective radiation emitter 202, and projected onto the contamination receiving surface of the dummy element 201 as well. In the present embodiment, the second radiation beam is being transmitted by the dummy element 201, towards a suitable radiation detector 306. Alternatively, the second radiation beam can be reflected by the dummy element towards a suitable radiation detector (not shown). From the detection of the second radiation beam, it can be evaluated whether the radiation receiving surface of the dummy element 201 has been contaminated, for instance by compounds that have been fixed to that surface under the influence of the second radiation beam In an aspect of the invention, said dummy element is a quartz crystal monitor or a surface acoustic wave detector. Such a crystal monitor or wave detector can also monitor, whether its contamination receiving surface has been contaminated.

Figure 5:
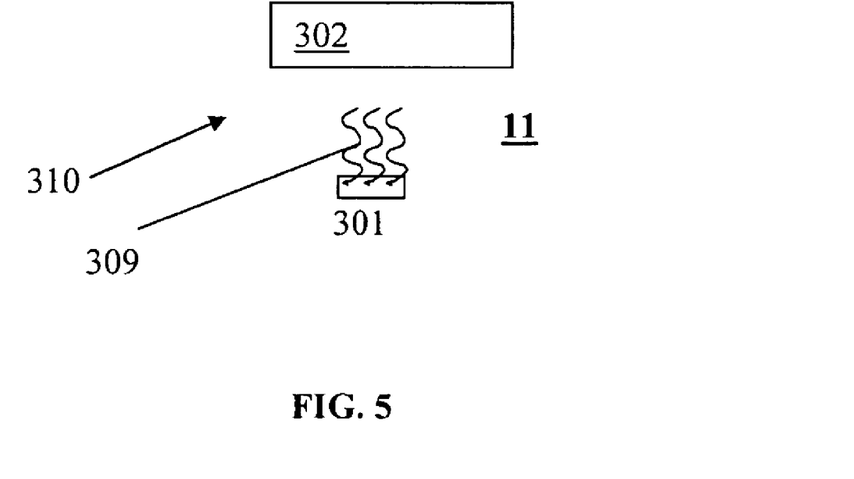
FIG. 5 schematically shows a fourth embodiment of a contamination monitoring device.

FIG. 5 schematically shows an embodiment of a contamination monitoring device 310, comprising a quartz crystal monitor 301. Alternatively, the device can include a surface acoustic wave detector instead of the quartz crystal monitor.

The quartz crystal monitor 301 of the embodiment of FIG. 5 has at least one contamination receiving surface, which contamination receiving surface is in contact with the interior apparatus space 11—to be monitored—during use. The monitoring device 310 includes at least one emitter 302 configured to emit a second radiation beam 309. The second radiation beam 309 is projected at least partially onto the contamination receiving surface of the quartz crystal monitor 301 during use. The quartz crystal monitor 301 can detect whether the at least one contamination receiving surface has been contaminated. In the embodiment of FIG. 5, said dummy element is the quartz crystal monitor, wherein the dummy element/quartz crystal monitor also serves as said detector during use. The second radiation beam 309 can, for example, be specifically chosen to modify or crack at least one species into one or more compounds. For example, the second radiation beam 309 can be of a radiation type which can crack hydrocarbons, for example to carbonize contamination onto the quartz crystal monitor 301. In one embodiment of the invention, for accurate measurement using the quartz crystal monitor 301, the radiation second beam 309 can be switched off at certain measurement periods.

Figure 6:
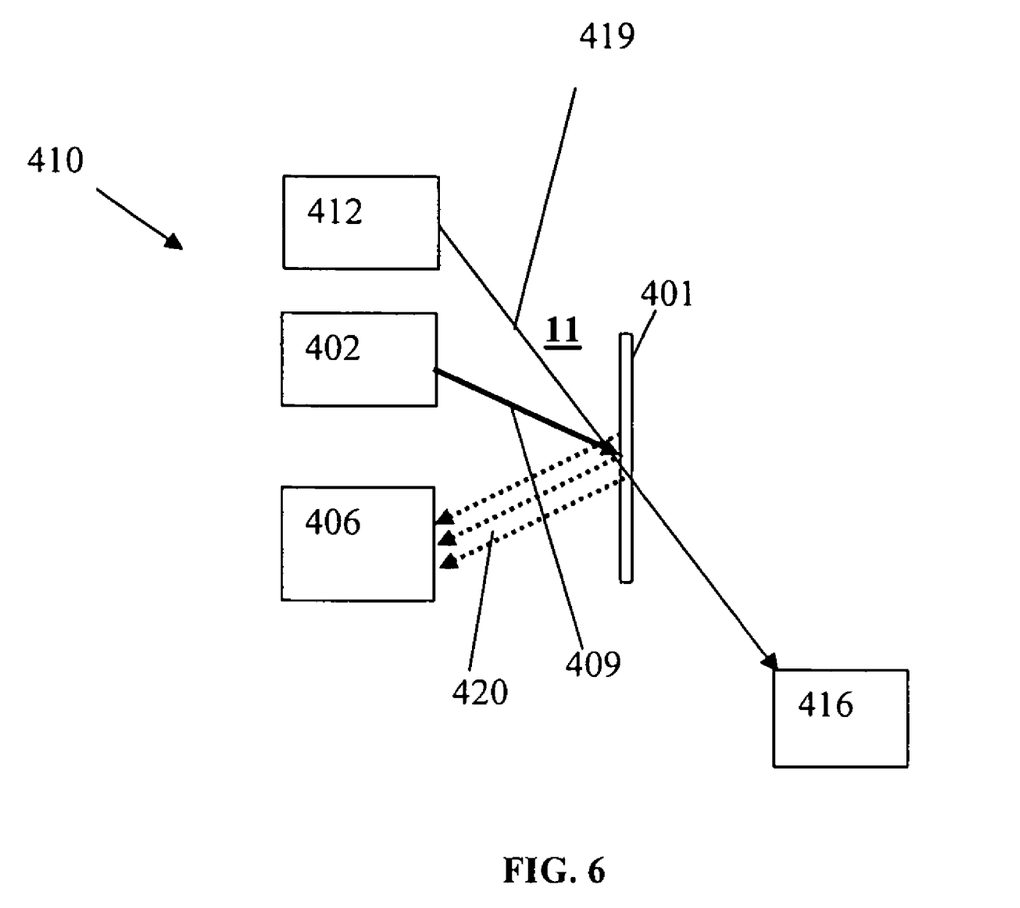
FIG. 6 schematically shows a fifth embodiment of a contamination monitoring device.

FIG. 6 schematically shows a fifth embodiment of a contamination monitoring device. In the embodiment of FIG. 6, the lithographic apparatus includes at least one monitoring device 410 which is configured to detect at least one contamination species. The monitoring device includes at least one dummy element 401 having at least one contamination receiving surface. The contamination receiving surface is in contact with said apparatus interior space 11 during use. The at least one monitoring device includes at least one emitter 402 configured to emit an electron beam 409, which electron beam 409 is projected at least partially onto the contamination receiving surface of said dummy element 401 during use. The electron beam 409 can, for example, crack hydrocarbon contamination onto the surface of the dummy element 401.

The monitoring device also includes a electron detector 406 which is constructed to detect whether the at least one contamination receiving surface of the dummy element has been contaminated. The detector 406 can, for example, be constructed to detect secondary electrons 420, which secondary electrons 420 can be emitted and/or reflected by said contamination receiving surface as a result of projecting said electron beam onto that surface. The amount of secondary electrons 420, being detected by the electron detector 406, can be used as an indication of the presence of contamination on the dummy element 401.

Alternatively, for example instead of the electron beam emitter 402 and electron detector 406, the emitter can be configured to emit an ionising beam, whereas the detector can be an ion detector. For example, the emitter can be an EUV beam emitter. Also, the detector can be an ion detector, which can detect ions, which ions can be emitted and/or reflected by said contamination receiving surface as a result of projecting said ionising beam onto that surface.

Also, the apparatus can include at least a second emitter 412 configured to emit a fourth radiation beam 419, wherein the wavelength of the fourth radiation beam differs from the wavelength of the second radiation beam, wherein the fourth radiation beam is also projected at least partially onto the contamination receiving surface of said dummy element during use, wherein a further detector 416 is arranged to receive a part of said fourth radiation beam 419 which is being transmitted and/or reflected by said dummy element 401 during use. Radiation of said at least fourth radiation beam 419 can be selected from the group consisting of the following radiation types: visible light, infra red light, ultra violet light, Deep UV light, extreme ultra-violet light and microwave radiation, or from other radiation types. The further detector 416 can detect the fourth radiation beam 419, to measure changes of radiation absorption. The amount of radiation of the fourth radiation beam, being detected by the further detector 416, can also be used as an indication of the presence of contamination on the dummy element 401.

Besides, according to an aspect of the invention, the sensitivity of the monitoring device 10, 110, 210, 310, 410 can be enhanced, by using a completely different duty cycle for the said second, third and/or fourth radiation beam that leads to contamination conversion, for example carbonization, for example of absorbed $C_xH_y$ molecules. For example, when a continuous radiation source is used as a second, third or fourth radiation beam, the reaction and/or modification process for some contamination species (volatile species) will be enhanced compared to a pulsed first radiation beam.

Figure 7:
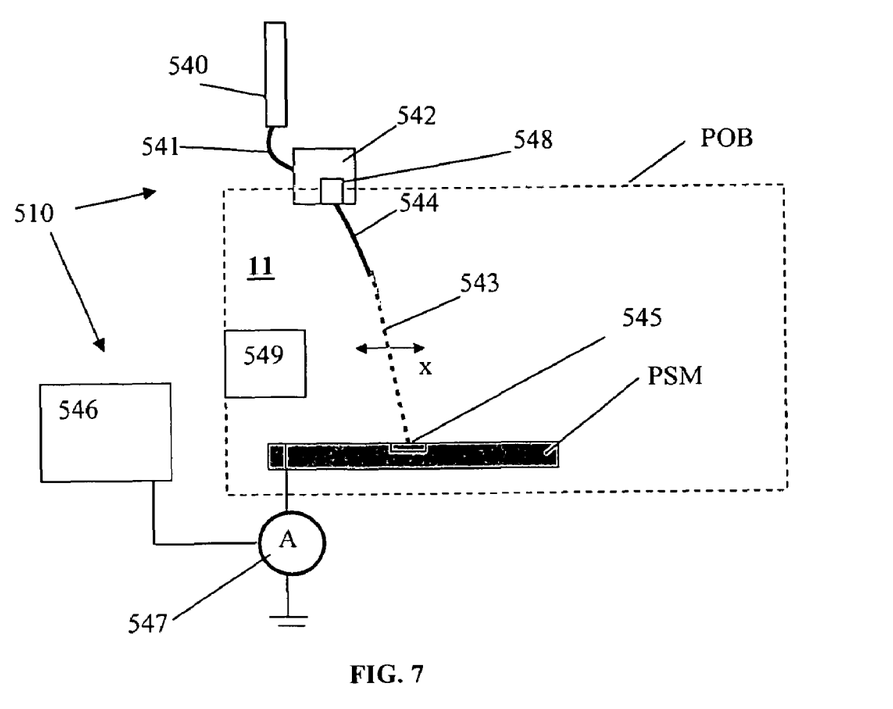
FIG. 7 depicts a sixth embodiment of the invention.

In another aspect of the invention, a lithographic apparatus can include at least one monitoring system 510 for monitoring contamination, as is shown schematically in FIGS. 1 and 7. The monitoring system 510 can be configured to monitor contamination of at least one optical element PSM of the projection system PS, which optical element PSM is located in or near an interior space 11 of the lithographic apparatus. The optical element PSM can be, for example, a mirror which receives said first radiation beam PB during a lithographic process. For example, said mirror PSM includes at least one mirror surface to reflect said first radiation beam PB. Parts of this monitoring system 510 can be located in various locations of the apparatus, for example in or near the projection system, in the projection optics box POB, in the illuminator IL or in other locations of the apparatus.

As is depicted in FIG. 7, in an aspect of the invention, the contamination monitoring system 510 can include: at least one second radiation source 540 which is configured to emit a second radiation beam 543; a radiation beam controller 542 configured to direct the second radiation beam 543 towards different surface parts 545 of a surface of said optical element PSM; and at least one current detector 547 which is configured to detect electrical current, which current emanates from said surface parts 545 of said optical element PSM when that surface part 545 receives said second radiation beam 543. For example, the electrical current can arise in the optical element PSM via the photo-electric effect.

The second radiation source 540 can be designed in various ways. For example, the second radiation source 540 can be configured to emit a photon beam, electromagnetic beam, or electron beam. In an aspect of the invention, said second radiation source 540 is configured to emit a second radiation beam having a radiation energy that is at least 2 eV, or larger than 2 eV. This radiation energy is the energy of the individual photon or electron respectively. For example, said radiation source can be configured to emit a second radiation beam having a radiation energy in the range of about 2 eV–30 eV.

Also, for example, the second radiation beam can be of such an energy, that the second radiation beam does not lead to removal of material from the optical element PSM (for example, as in sputtering). Then, a relatively low-energy radiation can be produced with a relatively inexpensive, easy to generate and easy controllable radiation source 540. For example, the second radiation source 540 can be a laser, one or more lamps, or an other suitable type of radiation source. The above-mentioned energy of about 2 eV corresponds to a photon wavelength of about 600 nm. Thus, in the sixth embodiment, shown in FIG. 7, a second radiation beam with a wavelength of about 600 nm or a shorter wavelength can be used. For example, the second radiation beam 543 has a higher wavelength than EUV light. The second radiation beam 543 can then be controlled, for example, using relatively uncomplicated beam steering and/or beam transporting devices, such as one or more optical fibres 541, 544 and other devices.

In the FIG. 7 embodiment of the invention, a first radiation directing device 541 is provided for directing the second radiation beam from the second radiation source 540 to the radiation beam controller 542. This first radiation directing device 541 can be designed in various ways. For example, the radiation directing device 541 can be simply an optical fibre, or an other suitable device, depending on the type of radiation to be directed thereby. Alternatively, the radiation beam controller 542 and the radiation source 540 are integrated with one another, wherein no first radiation directing device is provided.

The radiation beam controller 542 can be configured to direct said second radiation beam at least to the surface area of said optical element, which surface area receives said first radiation beam PB during use. Thus, contamination of the surface area, which receives the first radiation beam PB during a lithographic process, can be monitored during use of the monitoring system 510. For example, said radiation beam controller 542 can be configured to direct the second radiation beam 543 onto a mirror surface of the optical element PSM.

The radiation beam controller 542 can include a scanning device 548, configured to scan said second radiation beam over a plurality of surface parts of said optical element PSM. In FIG. 7, scanning directions are schematically indicated by a double arrow x. Various scan directions can be provided, for example by scanning the second beam 543 along two orthogonal axes over the surface of the optical element PSM, such that the plurality of surface parts lie in a 2-dimensional scanning pattern, as will be clear to the skilled person.

The scanning device can be configured in various ways. The scanning device can include, for example, one or more controllable mirrors, a movable beam director, or an other suitable device. In the embodiment of FIG. 7, the scanning device comprises a second radiation directing device 541, for example an optical fibre, which is movable to scan the second radiation beam 543 over the desired surface part of the optical element PSM. For example, in case the first radiation beam PB illuminates a first surface area of said optical element during lithography, said radiation beam controller 542 can be configured to scan the second radiation beam 543 at least over said first surface area of the optical element PSM.

The at least one detector 547 can be configured in various ways. For example, the detector 547 can be electrically connected to said optical element PSM, to receive electrical current therefrom. For example, the electrical connection between the current detector 547 and the optical element PSM can comprise suitable wiring, a current multiplier and/or other suitable electrical connection means. Alternatively, a current detector 549 can be configured to receive secondary electrons from said optical element PSM, which secondary electrons can emanate from each of said plurality of surface parts 545 of said optical element when that surface part 545 receives said second radiation beam. Also, in an embodiment of the invention, an electrical field can be created above the optical element PSM in order to make the measurement less sensitive to fields created in the measurement process, and to make the emission of secondary electrons more effective.

The monitoring system 510 can include at least one processor 546 which is configured to detect deviations or changes of the current, measured by said at least one detector.

The processor 546 can also be configured to process and/or store measurement results, which results include: electrical current measured by said detector when said second radiation beam is being directed at said at least one surface part of said optical element; and the respective location of said surface part of said optical element.

In the embodiment of FIG. 7, said various functions can be incorporated in a single processor 546. To the skilled person, it will be clear that more than one processor can be included to perform different operations and/or provide different functions. Each such processor 456 can be configured in various ways. A computer program product can be provided, comprising computer code portions, configured to be run on the processor 546 to provide certain operations and/or functions. Besides, as an example, said current detector 547 and the processor 546 may be integrated with one another.

During use, in a method for monitoring contamination of the optical element PSM, the second radiation beam 543 can be projected subsequently onto the plurality of surface parts 545 of said optical element PSM, to generate an electrical monitoring current in the element PSM.

The second radiation beam 543 can be scanned over at least part of said optical element by said beam controller 542, to monitor contamination of the plurality of surface parts. Also, in the present embodiment, the second beam 543 is not being projected onto said substrate W.

For example, the method for monitoring contamination can be part of a lithographic device manufacturing method which comprises: providing a projection system which projects a first radiation beam PB onto a target portion of a substrate, the projection system including at least one optical element PSM.

For example, said first radiation beam PB can illuminate a first surface area of said optical element PSM during the lithographic process, wherein a second surface area of said optical element PSM is illuminated by said second radiation beam 543 during the contamination monitoring. In an embodiment, said second surface area can be a small section of said first surface area, for example to pinpoint a location of surface contamination.

Further, said second radiation beam 543 can be scanned at least over the same surface area of the optical element PSM, as an surface area that receives said first radiation beam PB during said lithographic process.

The scanning of the optical element PSM by the second radiation beam can be performed at various instances, for example before and/or after a lithographic projection process is being performed using the optical element PSM. For example, when the radiation source SO is a pulsed source that emits a pulsed first radiation beam, the scanning of the optical element PSM by the second radiation beam can be performed between the periods when the first radiation beam pulses are being projected thereon. First and second radiation beam pulses can be, for example, out-of-sync with respect of one another during use. Also, the scanning of the optical element PSM by the second radiation beam 543 can be performed before, during and/or after a cleaning process to clean the optical element PSM, for example a cleaning process to remove carbon contamination from that element PSM.

During a contamination monitoring method, the generation of current in the optical element PSM can simply take place via the photo electric effect. The invention makes use of the fact that materials can emit electrons when being illuminated by photons. To the skilled person it will be clear, that this can depend on quantum yields, absorbance of the materials, and the electrical field near the material. For example, electrons can originate from the top few nanometers of the surface parts 545 of the optical element PSM, when being irridiated. The number of generated electrons can depend on the amount of photon absorption, which depends on the type of material present at the surface of the optical element PSM. The surface of the optical element can include, for example, Ruthenium, Iridium, Silicon, Molybdenum, Rhodium, Paladium, Gold, Zirconium, Niobium or other suitable materials.

During use of the embodiment of FIG. 7, said electrical monitoring current is measured by the current detector 547. The monitoring current can be the total current that runs through the optical element PSM. The monitoring current can include a current of secondary electrons, which secondary electrons can emanate from each of said plurality of surface parts 545 of said optical element when that surface part 545 receives said second radiation beam. Then, at least the following measurement results can being processed and/or stored by said processor 546: the monitoring current measured when said second radiation beam 543 is being directed at said surface of said optical element; and the respective surface part of said optical element.

Figure 8A:
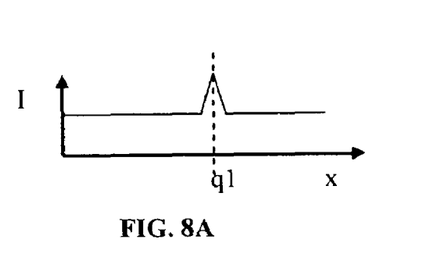
FIGS. 8A and 8B schematically depict measurement results.
Figure 8B:
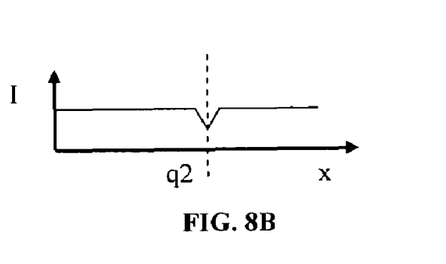

Also, deviations or changes of the monitoring current can be detected by said processor 546. Such deviations are depicted in FIGS. 8A and 8B. FIGS. 8A and 8B show the detected monitoring current I as function of the scanning location x at which the second radiation beam 543 intersects the surface of the optical element PSM.

Figure 9:
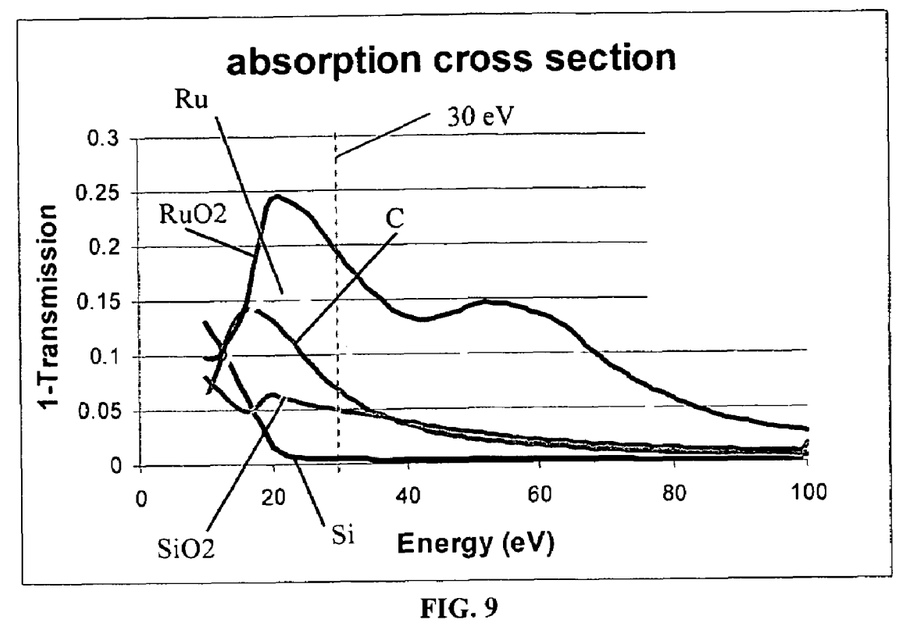
FIG. 9 depicts a graph showing photon absorption cross section as a function of photon energy for different materials.

As an example, during use, the second radiation beam 543 is a photon beam having an energy of about 30 eV, whereas the surface material of the optical element PSM consists substantially of Ruthenium. FIG. 9 shows the dependence of photon absorption as a function of the energy, for the materials Si, C, Ru, RuO2 and SiO2. From FIG. 9 it follows that, in case the surface of the optical element PSM substantially contains Ru, and the photon energy is about 30 eV, a carbon contamination of that surface will lead to less photon absorption and therefore to less electron emission. Any oxidation of the Ru-surface (to RuO2) will lead to more photon absorption and therefore to more electron emission (at the same photon energy).

In the detection result shown in FIG. 8A, the monitoring current I increases at a certain surface location q1 of the optical element PSM. Following from the above and FIG. 9, this current increase can be explained by a local oxidation of the surface of the optical element PSM.

In the result of FIG. 8B, the monitoring current I decreases at a certain surface location q2 of the optical element PSM. Following from the above and FIG. 9, this current decrease can be explained by a local carbonation of the surface of the optical element PSM.

In an aspect of the invention, after a certain type of degradation/contamination of the optical element PSM has been detected, for example degradation due to either carbonization or oxidation of the optics surfaces, appropriate action can be taken. For example, the locally detected contamination can be submitted to a local cleaning treatment, and/or the contaminated optical element PSM can be removed or replaced. Therefore, undesired transmission losses or reflection losses of overall projection system can be prevented, or detected at an early stage.

For example, degradation of each individual optical element of the projection system can be monitored, for example to decide, which optical element needs to be replaced or cleaned. To this aim, the lithographic apparatus can include one or more of the contamination monitoring apparatus.

In an aspect of the invention, local information can be obtained by illumination of a small part of the optical element, and measuring a resulting current. For example, as follows from the above, a scanning of the surface and a measuring of the current provides information whether the degradation of the surface is due to carbon or oxidation. In an embodiment, scanning of the surface of the optical element can be done with light of any wavelength, provided that the photon energy is large enough to provide electrons with enough energy to overcome the work function, thus leave the surface. An example: suppose that the mirror is locally contaminated, and one scans over the contaminated area with light of 30 eV. By going from a clean area of the surface to a contaminated area, the resulting current changes. When the current drops, this can mean that the surface is carbonated. When the current increases, this can indicate oxidation. This method can be applied as well during cleaning of carbon.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength lower than 20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

Besides, various combinations of different embodiments described above and in the figures and/or the claims can be made. For example, one or more embodiments according to or similar to any of FIGS. 2-6 can be used also in combination with an embodiment according or similar to that of FIG. 7.

What is claimed is:

1. A lithographic apparatus, comprising:
   a projection system configured to project a first radiation beam onto a target portion of a substrate; and
   at least one monitoring device configured to detect at least one contamination species in an interior space of the apparatus, said monitoring device comprising
      at least one dummy element having at least one contamination receiving surface, said contamination receiving surface being in contact with said interior space;
      at least one emitter configured to emit a second radiation beam, said second radiation beam being directed at least partially onto the contamination receiving surface of said dummy element, the second radiation beam incident on at least two distinct locations, exposed to the at least one contamination species, of said at least one dummy element; and
      a detector constructed and arranged to detect whether the at least one contamination receiving surface of the dummy element has been contaminated.

2. An apparatus according to claim 1, wherein the radiation of said at least second radiation beam is selected from the group consisting of the following radiation types: visible light, infra red light, ultra violet light, Deep UV light, extreme ultra-violet light, and microwave radiation.

3. An apparatus according to claim 1, wherein said emitter is a laser.

4. An apparatus according to claim 1, wherein said emitter is an electron beam emitter.

5. An apparatus according to claim 1, wherein said dummy element is a quartz crystal monitor or surface acoustic wave detector, which also serves as said detector.

6. A lithographic apparatus comprising:
   a projection system configured to project a first radiation beam onto a target portion of a substrate; and
   at least one monitoring device configured to detect at least one contamination species in an interior space of the apparatus, said monitoring device comprising
      at least one dummy element having at least one contamination receiving surface, said contamination receiving surface being in contact with said interior space;
      at least one emitter configured to emit a second radiation beam, said second radiation beam being projected at least partially onto the contamination receiving surface of said dummy element; and
      a detector constructed and arranged to detect whether the at least one contamination receiving surface of the dummy element has been contaminated,
   wherein said dummy element is at least partially transparent to the radiation of said at least second radiation beam, and
   wherein the at least one dummy element is constructed to provide an array of contamination receiving surfaces, and wherein at least part of said at least second radiation beam passes through all of the contamination receiving surfaces of said array at least once.

7. An apparatus according to claim 6, including a plurality of said dummy elements for providing a plurality of contamination receiving surfaces that are spaced-apart from each other, and wherein contamination receiving surfaces of neighbouring dummy elements are located opposite one another.

8. An apparatus according to claim 1, including at least one radiation reflector which is arranged to reflect radiation of said at least second radiation beam at least partially towards said contamination receiving surface of said dummy element.

9. A lithographic apparatus comprising:
a projection system configured to project a first radiation beam onto a target portion of a substrate; and
at least one monitoring device configured to detect at least one contamination species in an interior space of the apparatus, said monitoring device comprising
at least one dummy element having at least one contamination receiving surface, said contamination receiving surface being in contact with said interior space;
at least one emitter configured to emit a second radiation beam, said second radiation beam being projected at least partially onto the contamination receiving surface of said dummy element; and
a detector constructed and arranged to detect whether the at least one contamination receiving surface of the dummy element has been contaminated,
wherein said dummy element is located between at least two radiation reflectors, and wherein the reflectors are arranged to reflect radiation of said second radiation beam towards each other, through said dummy element.

10. An apparatus according to claim 1, wherein said contamination receiving surface of said dummy element is configured to reflect substantially all radiation of said second radiation beam.

11. An apparatus according to claim 1, wherein said detector is arranged to receive said second radiation beam after the second radiation beam has been transmitted and/or reflected at least once by the contamination receiving surface of said dummy element.

12. An apparatus according to claim 1, wherein said detector includes at least one photo diode.

13. An apparatus according to claim 1, wherein said detector is constructed to detect electrons.

14. An apparatus according to claim 1, wherein the monitoring device includes a thermal controller configured to control the temperature of said dummy element.

15. An apparatus according to claim 14, wherein the thermal controller is arranged to cycle the temperature of said dummy element between a plurality of monitoring temperatures.

16. An apparatus according to claim 1, wherein said contamination species includes hydrocarbon contamination.

17. An apparatus according to claim 1, wherein said contamination species includes water.

18. An apparatus according to claim 1, wherein said dummy element is located inside an optical box, said optical box including at least part of said projection system.

19. An apparatus according to claim 1, wherein said monitoring surface of said dummy element includes the same material as a radiation receiving surface of said projection system.

20. A lithographic apparatus, comprising:
a projection system configured to project a first radiation beam onto a target portion of a substrate; and
at least one monitoring device configured to detect at least one contamination species in an interior space of the apparatus, said monitoring device comprising
at least one dummy element having at least one contamination receiving surface, which contamination receiving surface is in contact with said interior space and not exposed to the first radiation beam;
at least one emitter configured to emit an electron beam or ionizing beam, said electron beam or ionizing beam being projected at least partially onto the contamination receiving surface of said dummy element; and
a detector constructed and arranged to detect whether the at least one contamination receiving surface of the dummy element has been contaminated.

21. An apparatus according to claim 20, wherein said detector is constructed to detect secondary electrons or ions, said secondary electrons or ions being emitted and/or reflected by said contamination receiving surface as a result of projecting said electron beam or ionizing beam onto that surface.

22. An apparatus according to claim 20, further comprising at least a second emitter configured to emit at least a fourth radiation beam, wherein the wavelength of the fourth radiation beam differs from the wavelength of the second radiation beam, wherein the fourth radiation beam is also projected at least partially onto the contamination receiving surface of said dummy element, wherein a detector is arranged to receive a part of said fourth radiation beam which is being transmitted and/or reflected by said dummy element, and wherein radiation of said at least fourth radiation beam is selected from the group consisting of the following radiation types: visible light, infra red light, ultra violet light, Deep UV light, extreme ultra-violet light and microwave radiation.

23. A lithographic apparatus, comprising:
a plurality of optical elements configured to project a first radiation beam onto a target portion of a substrate;
at least one radiation source configured to emit a second radiation beam;
a radiation beam controller configured to direct the second radiation beam onto at least two different locations of at least one of said optical elements; and
at least one detector configured to detect electrical current, which current emanates from said at least two different locations of said optical element when that locations interact with said second radiation beam.

24. An apparatus according to claim 23, wherein the radiation beam controller is configured to direct said second radiation beam at least to the surface area of said optical element, which surface area is configured to receive said first radiation beam.

25. An apparatus according to claim 24, including at least one processor configured to detect deviations or changes of the current, measured by said at least one detector.

26. An apparatus according to claim 23, wherein the radiation beam controller includes a scanning device, configured to scan said second radiation beam over a plurality of surface parts of said optical element.

27. An apparatus according to claim 26, including at least one processor configured to detect deviations or changes of the current, measured by said at least one detector.

28. An apparatus according to claim 23, including at least one processor configured to process and/or store measurement results, said results including an electrical current measured by said detector when said second radiation beam is being directed at said at least two different locations of said optical element; and the respective positions of the at least two different locations of said optical element.

29. An apparatus according to claim 23, wherein said radiation source is configured to emit a second radiation beam having a radiation energy of at least 2 eV.

30. An apparatus according to claim 29, wherein said radiation source is configured to emit a photon beam as the second radiation beam.

31. An apparatus according to claim 29, wherein said radiation source is configured to emit an electron beam as the second radiation beam.

32. An apparatus according of claim 23, wherein said radiation source is configured to emit a second radiation beam having a radiation energy in the range of about 2 eV-30 eV.

33. An apparatus according to claim 23, wherein said optical element is a mirror that includes at least one mirror surface to reflect said first radiation beam, and wherein said radiation beam controller is configured to direct the second radiation beam onto said mirror surface of the optical element.

34. An apparatus according to claim 23, wherein said first radiation beam illuminates a first surface area of said optical element, and wherein said radiation beam controller is configured to scan the second radiation beam at least over said first surface area of the optical element.

35. An apparatus according to claim 23, wherein said detector is electrically connected to said optical element to receive said electrical current therefrom.

36. An apparatus according to claim 23, wherein said detector is configured to receive secondary electrons from said optical element, which secondary electrons emanate from each of said plurality of locations of said optical element when that locations interact with said second radiation beam.

* * * * *